(12) United States Patent
Chan et al.

(10) Patent No.: US 12,113,328 B2
(45) Date of Patent: *Oct. 8, 2024

(54) OPTICAL SUBASSEMBLY HAVING SIDE-EMITTING OPTICAL FIBER COUPLED TO HIGH-ENERGY UV-C LASER DIODE

(71) Applicant: The Boeing Company, Chicago, IL (US)

(72) Inventors: Eric Y. Chan, Mercer Island, WA (US); Dennis G. Koshinz, Bellevue, WA (US); Kim Quan Anh Nguyen, Seattle, WA (US); Lyndon G. Mazon, Lynnwood, WA (US)

(73) Assignee: The Boeing Company, Arlington, VA (US)

( * ) Notice: Subject to any disclaimer, the term of this patent is extended or adjusted under 35 U.S.C. 154(b) by 651 days.

This patent is subject to a terminal disclaimer.

(21) Appl. No.: 17/395,976

(22) Filed: Aug. 6, 2021

(65) Prior Publication Data

US 2022/0102937 A1     Mar. 31, 2022

Related U.S. Application Data

(60) Provisional application No. 63/084,469, filed on Sep. 28, 2020.

(51) Int. Cl.
  *A61L 2/10*  (2006.01)
  *G02B 6/10*  (2006.01)
  (Continued)

(52) U.S. Cl.
  CPC ............ *H01S 5/02251* (2021.01); *A61L 2/10* (2013.01); *G02B 6/102* (2013.01);
  (Continued)

(58) Field of Classification Search
  CPC .......... A61L 2/10; A61L 9/20; A61L 2202/11; A61L 2209/12; H01S 5/02251;
  (Continued)

(56) References Cited

U.S. PATENT DOCUMENTS

| | | |
|---|---|---|
| 8,582,943 B2 | 11/2013 | Alkemper et al. |
| 9,329,318 B2 | 5/2016 | Russert |

(Continued)

OTHER PUBLICATIONS

Zhang et al., "A 271.8 nm deep-ultraviolet laser diode for room temperature operation", Applied Physics Express, 12, Nov. 7, 2019.

(Continued)

*Primary Examiner* — Lessanework Seifu
(74) *Attorney, Agent, or Firm* — Ostrager Chong Flaherty & Broitman P.C.

(57) ABSTRACT

An optical subassembly includes a housing, a laser package, and first and second end sections of side-emitting optical fiber. The housing defines first, second, and third channels which extend from a central space. The laser package is affixed to the third channel and comprises an edge-emitting UV-C laser diode disposed in the central space and having first and second edges. The first end section of side-emitting optical fiber is retained in the first channel and has a first end face which confronts the first edge. The second end section of side-emitting optical fiber is retained in the second channel and has a second end face which confronts the second edge. The housing further defines a fourth channel which extends from the central space. The optical subassembly further includes a transparent window seated in an opening of the fourth channel.

20 Claims, 14 Drawing Sheets

(51) Int. Cl.
*H01S 5/02251* (2021.01)
*H01S 5/02345* (2021.01)
*H01S 5/0237* (2021.01)
*H01S 5/024* (2006.01)
*H01S 5/026* (2006.01)
*H01S 5/042* (2006.01)
*H01S 5/343* (2006.01)

(52) U.S. Cl.
CPC ........ *H01S 5/02345* (2021.01); *H01S 5/0237* (2021.01); *H01S 5/02469* (2013.01); *H01S 5/026* (2013.01); *H01S 5/0428* (2013.01); *H01S 5/34333* (2013.01); *A61L 2202/11* (2013.01)

(58) Field of Classification Search
CPC ............... H01S 5/02345; H01S 5/0237; H01S 5/02469; H01S 5/026; H01S 5/0428; H01S 5/34333; G02B 6/102
See application file for complete search history.

(56) References Cited

U.S. PATENT DOCUMENTS

| | | |
|---|---|---|
| 10,261,229 B2 | 4/2019 | Woelfing et al. |
| 10,261,230 B2 | 4/2019 | Gaydoul et al. |
| 10,569,699 B2 | 2/2020 | Schabacker et al. |

OTHER PUBLICATIONS

Lawal et al., "UV-C LED Devices and Systems: Current and Future State", IUVA News, vol. 20, No. 1, Mar. 2018.
Schott HelioLine Datasheet, undated, but the disclosed product (High-quality Aviation approved side-emitting glass fiber cable) is prior art and the unknown month and year of date of first publication is not material.

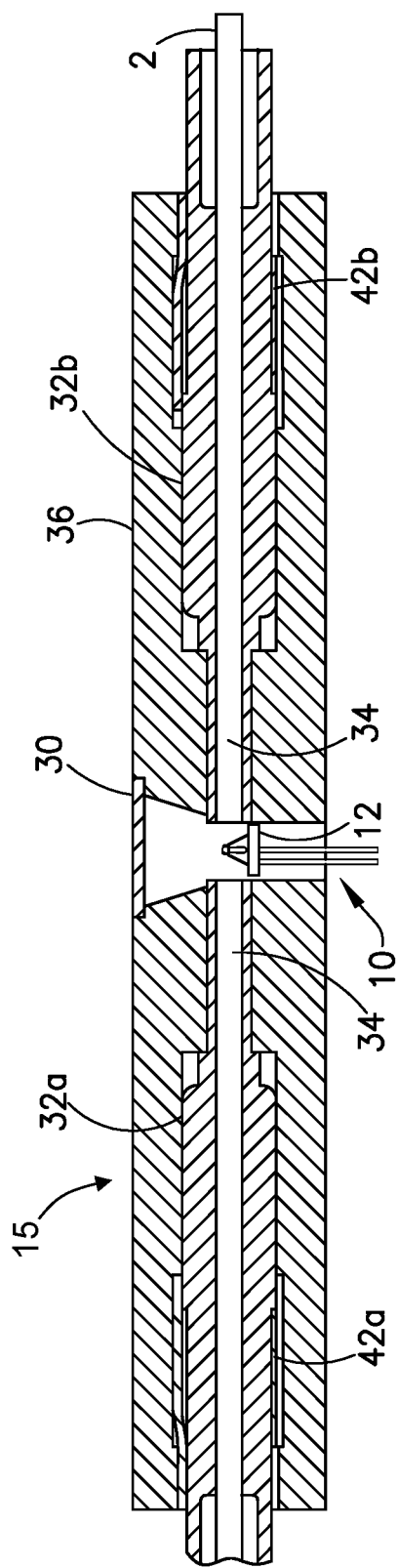
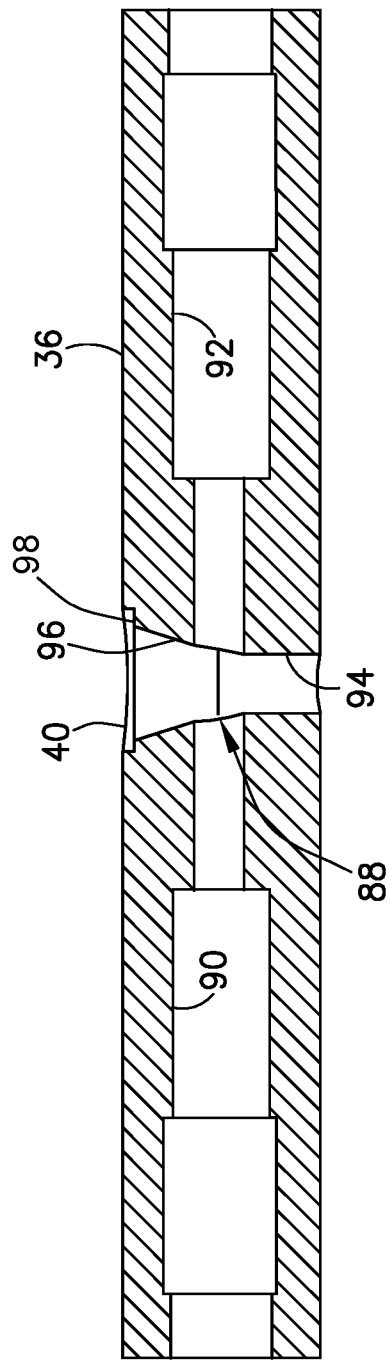

OPTICAL SUBASSEMBLY HAVING SIDE-EMITTING OPTICAL FIBER COUPLED TO HIGH-ENERGY UV-C LASER DIODE

RELATED PATENT APPLICATION

This application claims the benefit, under Title 35, United States Code, Section 119 (e), of U.S. Provisional Application No. 63/084,469 filed on Sep. 28, 2020.

BACKGROUND

This disclosure generally relates to design and fabrication of systems for destroying or inactivating pathogenic agents (such as bacteria, protozoans, and viruses). In particular, this disclosure relates to ultraviolet light-emitting assemblies for use in disinfection systems.

Ultraviolet germicidal irradiation is a disinfection method that uses ultraviolet C (UV-C) light to kill submicroscopic infectious agents and inactivate microorganisms. UV-C light has wavelengths in the range of 100-280 nm. According to the Centers for Disease Control and Prevention, the maximum bactericidal effect occurs at 240-280 nm. The application of UV-C light has proven to be effective in destroying submicroscopic infectious agents and inactivating microorganisms on surfaces.

Existing solutions use individual UV light-emitting diodes (LEDs) or mercury lamps as a source to perform disinfection. However, implementing a large number of UV LEDs and mercury lamps inside a commercial airplane is not very efficient for disinfection because UV LEDs are not emitting UV-C photons efficiently compared to a laser light source, whereas mercury lamps are not preferred light sources because the lamps contain mercury, which is an environmental hazard. Besides, using individual LEDs and mercury lamps cannot cover a wide and lengthy area in a commercial airplane, and installing an LED array and mercury lamps in tight space locations inside a commercial airplane is expensive and may be impractical. Examples of such areas are the flight deck, lavatories, flight attendant stations, passenger cabin, cargo compartments, and electronics bays.

The cost of parking an airplane on the ground to undergo disinfection is large. Systems capable of assuring that the airplane is free of pathogens with very low cost of operation would be beneficial. Accordingly, an effective optical disinfection system that can quickly disinfect difficult-to-access areas inside an airplane without human intervention is desired.

SUMMARY

The subject matter disclosed in some detail below is directed to the implementation of high-energy optical disinfection systems inside a commercial airplane using highly efficient, flexible, and durable side-emitting optical fibers optically coupled to high-energy UV-C laser diodes to destroy submicroscopic infectious agents and inactivate microorganisms inside the airplane. With the high-energy UV-C laser diodes optically coupled to the side-emitting optical fibers, which can be easily routed to different areas inside the airplane, the high-energy UV-C laser light emitted from the side of the optical fiber will disinfect the airplane along a wide or long swath continuously without interruption. The proposed systems will assure that the airplane is free of pathogens with a very low cost of operation.

The embodiments of optical disinfection systems disclosed herein use high-efficiency side-emitting optical fiber to route UV-C laser light to different areas inside the airplane, such as the flight deck, lavatories, flight attendant stations, passenger cabin, cargo compartments, and electronics bays. A high-energy UV-C laser light source is selected which can be operated in a low-duty-cycle pulse mode, burst mode, or continuous mode to disinfect airborne or surface-borne pathogens (e.g., virus) inside the airplane.

As used herein, the term "optical fiber" has either of two meanings depending on the context in which the term is used. In some instances (for example, in the claims), the term is used without the preceding article "an" to refer to optical fiber in general as a type of structural element; in other instances, the term is used with the preceding article "an" to specifically refer to a single optical fiber. For avoidance of doubt, the term "optical fiber" without "an" (and without "a single"), as appears in the claims, should be construed to encompass at least a single optical fiber (e.g., formed as a loop with ends confronting opposite edges of a laser diode) or first and second optical fibers (e.g., having respective ends confronting opposite edges of a laser diode).

The benefits of using side-emitting optical fiber are manifold. Side-emitting optical fiber of relatively large diameter is very flexible and durable, and the cost of installing optical fiber in an airplane is relatively low. Side-emitting optical fiber can deliver UV-C light to a large area inside the airplane as compared to approaches using individual UV LEDs and mercury lamp sources. Side-emitting optical fiber can deliver UV-C laser light efficiently to difficult-to-access tight spaces or covered areas inside the airplane, thereby enhancing the efficiency of the disinfection process onboard the airplane without human intervention. The side-emitting optical fibers are optically coupled to UV-C laser diodes for continuous illumination, the individual assemblies being routed through selected areas inside the airplane to provide long-lasting disinfection.

In accordance with one embodiment, the high-power and high-energy UV-C laser diode is integrated into an optical subassembly designed for high-reliability commercial airplane applications. The optical subassembly integrates the UV-C laser diode and two side-emitting optical fibers. The UV-C laser diode is electrically coupled to laser diode driver electronics incorporated in an electronics housing. In accordance with one proposed implementation designed to kill virus, the laser diode is operated in pulse mode for effective disinfection, because fast laser pulses kill the virus faster in a shorter time than the virus reproduction time.

Although various embodiments of an optical subassembly having side-emitting optical fiber optically coupled to a UV-C laser diode will be described in some detail below, one or more of those embodiments may be characterized by one or more of the following aspects.

One aspect of the subject matter disclosed in detail below is an optical subassembly comprising: a housing that defines first, second, and third channels which extend from a central space; a laser package affixed to the third channel and comprising a UV-C laser diode chip disposed in the central space and having first and second edges; a first end section of side-emitting optical fiber retained in the first channel and having a first end face which confronts the first edge; and a second end section of side-emitting optical fiber retained in the second channel and having a second end face which confronts the second edge. In accordance with one embodiment, the housing further defines a fourth channel which extends from the central space and has an offset, the optical subassembly further comprising a transparent window seated on the offset.

Another aspect of the subject matter disclosed in detail below is a laser package comprising: a header base having first and second throughholes; a ground pin having one end connected to the header base; a heat sink having a top, a base, and first and second throughholes that pass through the base and not the top, the base of the heat sink being attached to the header base; an anode pin that passes through the first throughholes in the header base and heat sink with electrical insulation between the anode pin and the header base and heat sink; a cathode pin that passes through the second throughholes in the header base and heat sink with electrical insulation between the cathode pin and the header base and heat sink; a laser diode chip attached to the top of the heat sink, the laser diode chip being configured to emit UV-C laser light; a first wire that connects the UV-C laser diode chip to the anode pin; and a second wire that connects the UV-C laser diode chip to the cathode pin.

A further aspect of the subject matter disclosed in detail below is an optical disinfection system comprising: an electronics housing; a printed wiring board attached to the electronics housing and comprising a socket; a laser package plugged into the socket of the printed wiring board, the laser package comprising a laser diode chip configured to emit UV-C laser light; a first end section of a side-emitting optical fiber having a first end face; a first terminus surrounding the first end section; a second end section of a side-emitting optical fiber having a second end face; a second terminus surrounding the second end section; and an optical subassembly housing attached to the electronics housing, the optical subassembly housing having a first channel in which the first terminus is seated and a second channel in which the second terminus is seated, wherein the laser diode chip is disposed between the first and second end faces. In some embodiments, the first and second end faces are end faces of a single side-emitting optical fiber. In other embodiments, the first and second end faces are end faces of respective side-emitting optical fibers. In accordance with one proposed implementation, the optical subassembly housing has an opening overlying the laser diode chip, and the optical disinfection system further comprises a transparent window seated in the opening.

Yet another aspect of the subject matter disclosed in detail below is an assembly comprising: a printed wiring board comprising a socket; a laser package plugged into the socket of the printed wiring board, the laser package comprising a UV-C laser diode chip having first and second edges; a first end section of side-emitting optical fiber having a first end face; a second end section of side-emitting optical fiber having a second end face; and a housing which is configured to maintain the laser package and the first and second end sections of side-emitting optical fiber in fixed positional relationships such that the first end face confronts the first edge and the second end face confronts the second edge. The first and second end faces may be either end faces of a single side-emitting optical fiber or end faces of first and second side-emitting optical fibers.

Other aspects of an optical subassembly having side-emitting optical fiber optically coupled to a UV-C laser diode are disclosed and claimed below.

BRIEF DESCRIPTION OF THE DRAWINGS

The features, functions and advantages discussed in the preceding section can be achieved independently in various embodiments or may be combined in yet other embodiments. Various embodiments will be hereinafter described with reference to drawings for the purpose of illustrating the above-described and other aspects. None of the diagrams briefly described in this section are drawn to scale.

FIG. 10A is a diagram representing a sectional view of an optical subassembly that includes the components depicted in FIG. 9. Only the laser package and the optical fibers are not sectioned.

FIG. 10B is a diagram representing a sectional view of the OSA housing included in the optical subassembly depicted in FIG. 10A.

Reference will hereinafter be made to the drawings in which similar elements in different drawings bear the same reference numerals.

DETAILED DESCRIPTION

Illustrative embodiments of an optical subassembly having side-emitting optical fiber optically coupled to a UV-C laser diode are described in some detail below. However, not all features of an actual implementation are described in this specification. A person skilled in the art will appreciate that in the development of any such embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are three bands of UV light source available for disinfection: the UV-A, UV-B, and UV-C bands. But only the UV-C band in the wavelength range of 200 nm to 280 nm is effective for disinfection applications. Commercially available UV LEDs are mainly in the UV-A and UV-B bands. Also, an LED is not efficient in generating sufficiently high power to couple to an optical fiber for a long-distance disinfection application.

Using a laser to generate UV-C light has some challenges in device fabrication. UV-C light photons are higher energy than the UV-A and UV-B photons. Therefore, the light generated in the active layer of the laser diode is absorbed by the light-guiding layer above and below the active layer of the UV-C laser diode before it can be output to the edges of the laser diode.

To overcome the foregoing problem, the light-guiding layer of the UV-C laser diode must have a much higher band-gap than the active layer. The higher band-gap layers are difficult to fabricate because these layers have a much larger lattice constant (or size), which causes lattice mismatch with the laser substrate and the active layer. The lattice mismatch produces defects in the active layers which reduce the effective stimulated UV-C laser light emission in the laser structure.

Figure 1:
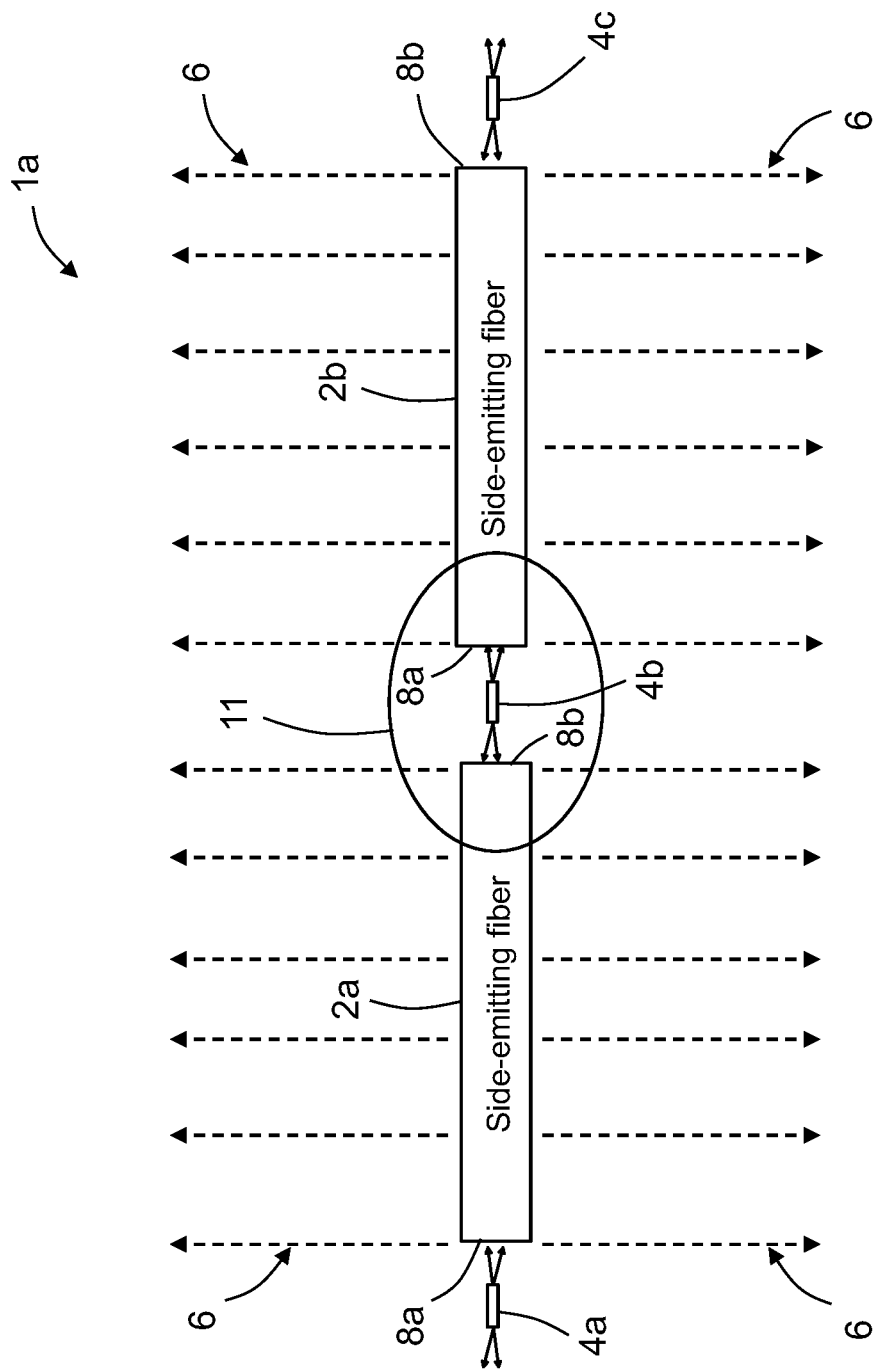
FIG. 1 is a diagram showing components of an optical disinfection system in which each side-emitting optical fiber receives UV-C laser light at opposing end faces from respective pairs of UV-C laser diodes.

FIG. 1 is a diagram showing components of an optical disinfection system 1 in which one side-emitting optical fiber 2a receives UV-C laser light at opposing end faces 8a and 8b from a first UV-C laser diode 4a (hereinafter "UV-C laser diode 4a") and a second UV-C laser diode 4b (hereinafter "UV-C laser diode 4b"), whereas another side-emitting optical fiber 2b receives UV-C laser light at opposing end faces 8a and 8b from UV-C laser diode 4b and a third UV-C laser diode 4c (hereinafter "UV-C laser diode 4c"). In accordance with one embodiment, the side-emitting optical fibers 2a and 2b are of a type having a scattering region surrounding the core (but inside the cladding) in which scattering particles are embedded in glass, and the UV-C laser diodes 4a-4c are of the edge-emitting type.

In accordance with one embodiment, each UV-C laser diode is an edge-emitting semiconductor chip with cleaved facets. The solid arrows emanating from the laser diodes depicted in FIG. 1 represent UV-C laser light 6 emitted from opposing edges of the semiconductor chip, which UV-C laser light enters the adjacent side-emitting optical fiber. For example, some UV-C laser light emitted by UV-C laser diode 4a enters one end of side-emitting optical fiber 2a and some UV-C laser light emitted by UV-C laser diode 4b enters the other end of side-emitting optical fiber 2a, while other UV-C laser light emitted by UV-C laser diode 4b enters one end of side-emitting optical fiber 2b and some UV-C laser light emitted by UV-C laser diode 4c enters the other end of side-emitting optical fiber 2b. As the UV-C laser light propagates inside the side-emitting optical fibers 2a and 2b, some of the UV-C laser light 6 is emitted out the sides of the fibers (represented by dashed arrows in FIG. 1). The optical fibers may be placed in strategic positions onboard an aircraft for the purpose of disinfecting space and surfaces in the path of the side-emitted UV-C laser light 6.

The interface 11 of UV-C laser diode 4b and side-emitting optical fibers 2a and 2b is outlined by an ellipse in FIG. 1. This disclosure proposes an optical subassembly (OSA) housing (not shown in FIG. 1, but described later with reference to FIGS. 9-12) which is designed to maintain the respective diode/fiber positional relationships at interface 11. More specifically, the UV-C laser diode 4b and side-emitting optical fibers 2a and 2b are seated in respective channels of the OSA housing so that respective maximum amounts of UV-C laser light emitted from opposing edges of UV-C laser diode 4b respectively enter side-emitting optical fibers 2a and 2b.

Figure 2:
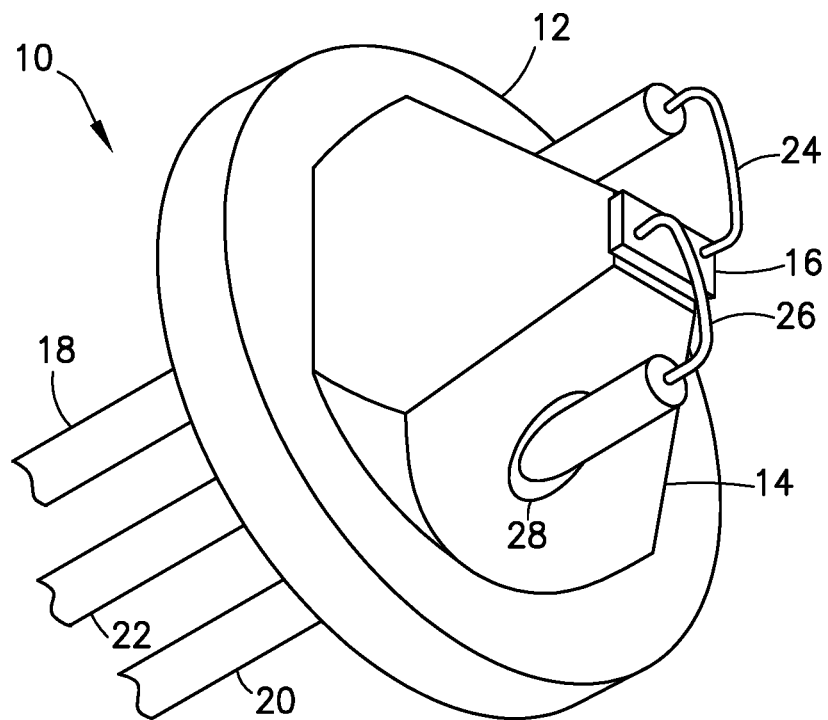
FIG. 2 is a diagram representing a three-dimensional view of a laser package that includes a UV-C laser diode mounted on top of a heat sink in accordance with one proposed implementation.

FIG. 2 is a diagram representing a three-dimensional view of a laser package 10 that includes a UV-C laser diode chip 16 mounted on top of a heat sink 14 in accordance with one proposed implementation. The laser package 10 further includes a Transistor Outline (TO) header having a header base 12. For example, the TO header may have the industrial standard designation "TO 18". The header base 12 has first and second throughholes. The laser package 10 further includes a ground pin 22 having one end connected to the bottom of the header base 12.

Still referring to FIG. 2, the heat sink 14 has a top, a base, and first and second throughholes that pass through the base and not the top. The base of the heat sink 14 is attached to the header base 12 such that the first and second throughholes of heat sink 14 respectively align with the first and second throughholes of header base 12. The laser package 10 further includes: (a) an anode pin 20 that passes through the first throughholes in the header base 12 and heat sink 14 with electrical insulation 28 between the anode pin 20 and the header base 12 and heat sink 14; and (b) a cathode pin 18 that passes through the second throughholes in the header base 12 and heat sink 14 with electrical insulation between the cathode pin 18 and the header base 12 and heat sink 14. The electrical insulation 28 which surrounds the embedded portions of the anode and cathode pins may be made of solder glass material.

As seen in FIG. 2, the UV-C laser diode chip 16 is attached to the top of the heat sink 14. The top of the heat sink 14 has a first surface area and the base of the heat sink has a second surface area greater than the first surface area. In accordance with one proposed implementation, the heat sink 14 is pyramid-shaped with a truncated top and truncated corners at the base of the heat sink 14.

A first wire 26 connects the UV-C laser diode chip 16 to the anode pin 20. A second wire 24 connects the UV-C laser diode chip 16 to the cathode pin 18. In accordance with at least some embodiments, the UV-C laser diode chip 16 is an edge-emitting laser diode configured to emit UV-C laser light. In accordance with one proposed implementation, the edge-emitting laser diode comprises a quantum well active layer and first and second waveguides disposed on opposite sides of the quantum well active layer (as will be described in more detail below with reference to FIG. 18).

Figure 3:
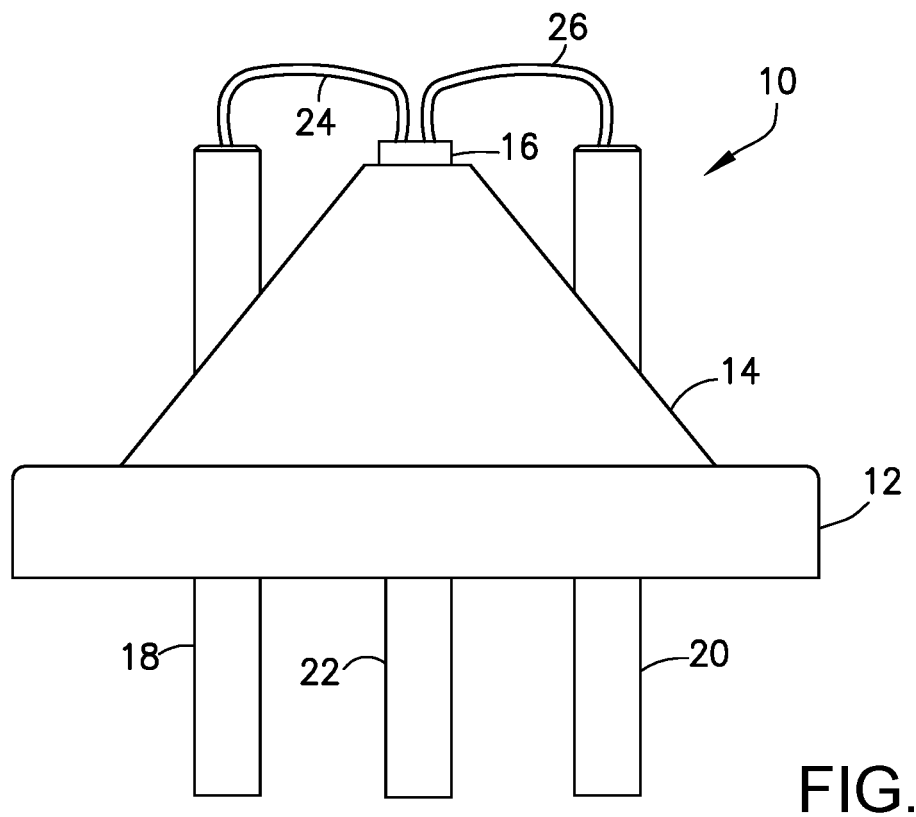
FIG. 3 is a diagram representing a side view of the laser package depicted in FIG. 2.
Figure 4:
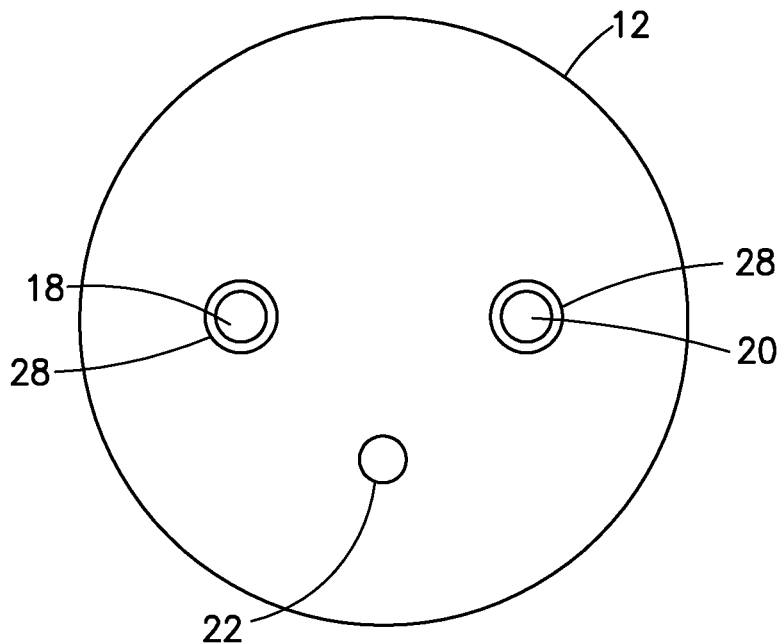
FIG. 4 is a diagram representing a bottom view of the laser package depicted in FIGS. 2 and 3 (the laser diode chip and heat sink are not visible in this view).
Figure 5:
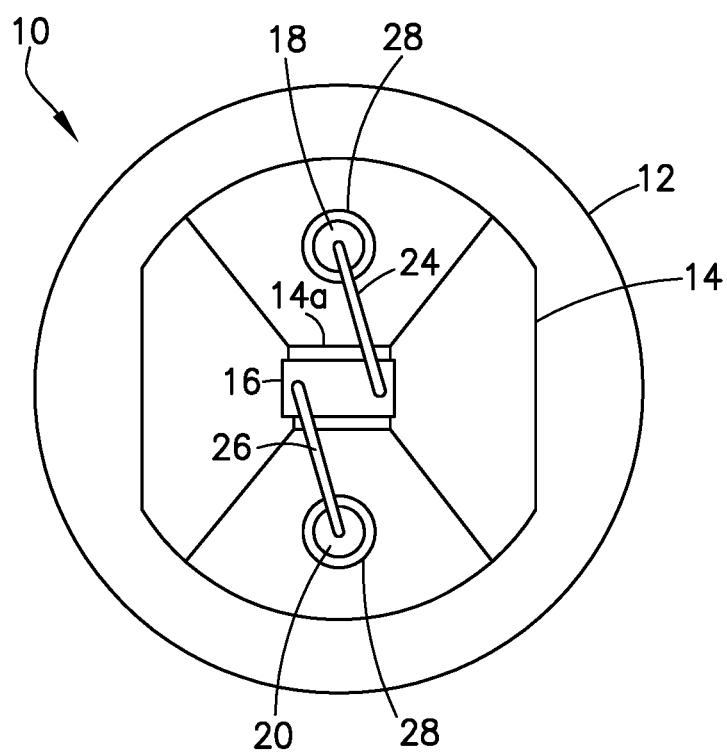
FIG. 5 is a diagram representing a top view of the laser package depicted in FIGS. 2-4.

The first step to fabricate the UV-C optical subassembly proposed herein is mounting the heat sink 14 on the header base 12. Then the UV-C laser diode chip 16 is attached on the top of the heat sink 14. The die of the UV-C laser diode chip 16 is bonded to the flat top of the heat sink 14 by eutectic gold-tin (AuSn) solder. Because gold-tin solder has a melting temperature greater than 300° C., the eutectic die bonding process assures that the laser diode is capable of operating at high temperatures with high reliability. Using a heat sink in the form of a pyramid which has a wide area on the bottom enhances the thermal conductivity of the heat sink 14 and lowers the laser diode's junction temperature during continuous operation. After the laser diode chip die bonding has been completed, the top side of the UV-C laser diode chip 16 is wire bonded to the cathode pin 18 and anode pin 20 of the TO header. More specifically, the p-contact pad on UV-C laser diode chip 16 is wire bonded to the anode pin 20; the n-contact pad on of UV-C laser diode chip 16 is wire bonded to the cathode pin 18. FIG. 3 is a side view of the UV-C laser package 10 depicted in FIG. 2. FIG. 4 is a bottom view of the TO header that is part of the UV-C laser package shown FIGS. 2 and 3 (the laser diode chip and heat sink are not visible in this view). FIG. 5 is a top view of the UV-C laser package 10 depicted in FIGS. 2 and 3 (the ground pin is not visible in this view).

Figure 6:
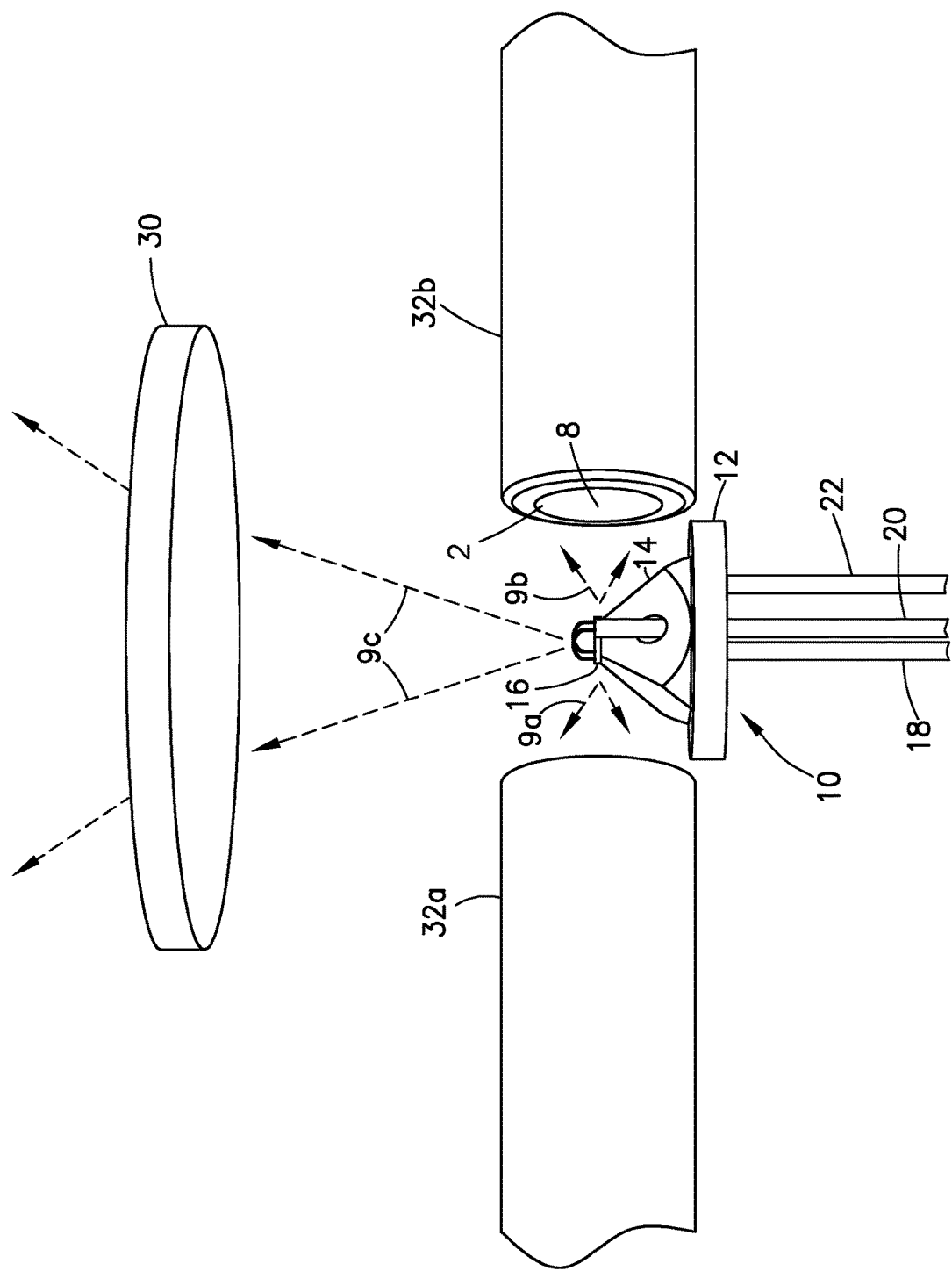
FIG. 6 is a diagram representing a three-dimensional view of some components of an optical subassembly in accordance with one embodiment. The housing of the optical subassembly has been omitted to reveal a laser package (of the type depicted in FIG. 2) situated between respective end faces of respective end sections of side-emitting optical fiber and beneath a transparent window. The dashed arrows represent UV-C laser light emitted by the laser diode.

FIG. 6 is a diagram representing a three-dimensional view of some components of an optical subassembly in accordance with one embodiment. The housing of the optical subassembly has been omitted to reveal a laser package 10 (of the type depicted in FIG. 2) situated between respective end faces of respective end faces 8 of side-emitting optical fiber 2 and beneath a transparent window 30. The end sections of side-emitting optical fiber 2 are seated in respective termini 32a and 32b. The end sections (not shown in FIG. 6, but see end sections 34 in FIGS. 9 and 10) may be sections at opposite ends of a single optical fiber in the shape of a loop or may be end sections of two different optical fibers (e.g., two coaxial optical fibers separated by a gap, the UV-C laser diode chip 16 being situated in the gap).

The dashed arrows in FIG. 6 represent UV-C laser light emitted by the UV-C laser diode chip 16. Some edge-emitted UV-C laser light 9a enters the side-emitting optical fiber seated in the terminus 32a at end face 8; other edge-emitted UV-C laser light 9b enters the side-emitting optical fiber seated in the terminus 32b at an end face which is not visible in FIG. 6; and some residual UV-C laser light 9c impinges on the transparent window 30 and is transmitted therethrough. The laser package 10, transparent window 30, and termini 32a and 32b are maintained in the respective positions depicted in FIG. 6 by an OSA housing (not shown in FIG. 6).

FIG. 6 shows placement of the UV-C laser package 10 so that the UV-C laser diode chip is aligned with two end faces 8 of side-emitting optical fiber 2 embedded inside respective termini 32a and 32b, with a transparent window 30 overlying the laser diode chip. More specifically, the respective axes of the two end sections 34 of side-emitting optical fiber 2 are aligned with respective edges on opposite sides of the UV-C laser diode chip. The transparent window 30 allows visual observation of the UV-C laser diode chip position and also allows residual UV-C light emission (UV-C laser light 6c in FIG. 6) from the top of the laser diode chip to radiate outward for the purpose of disinfection.

Figure 7:
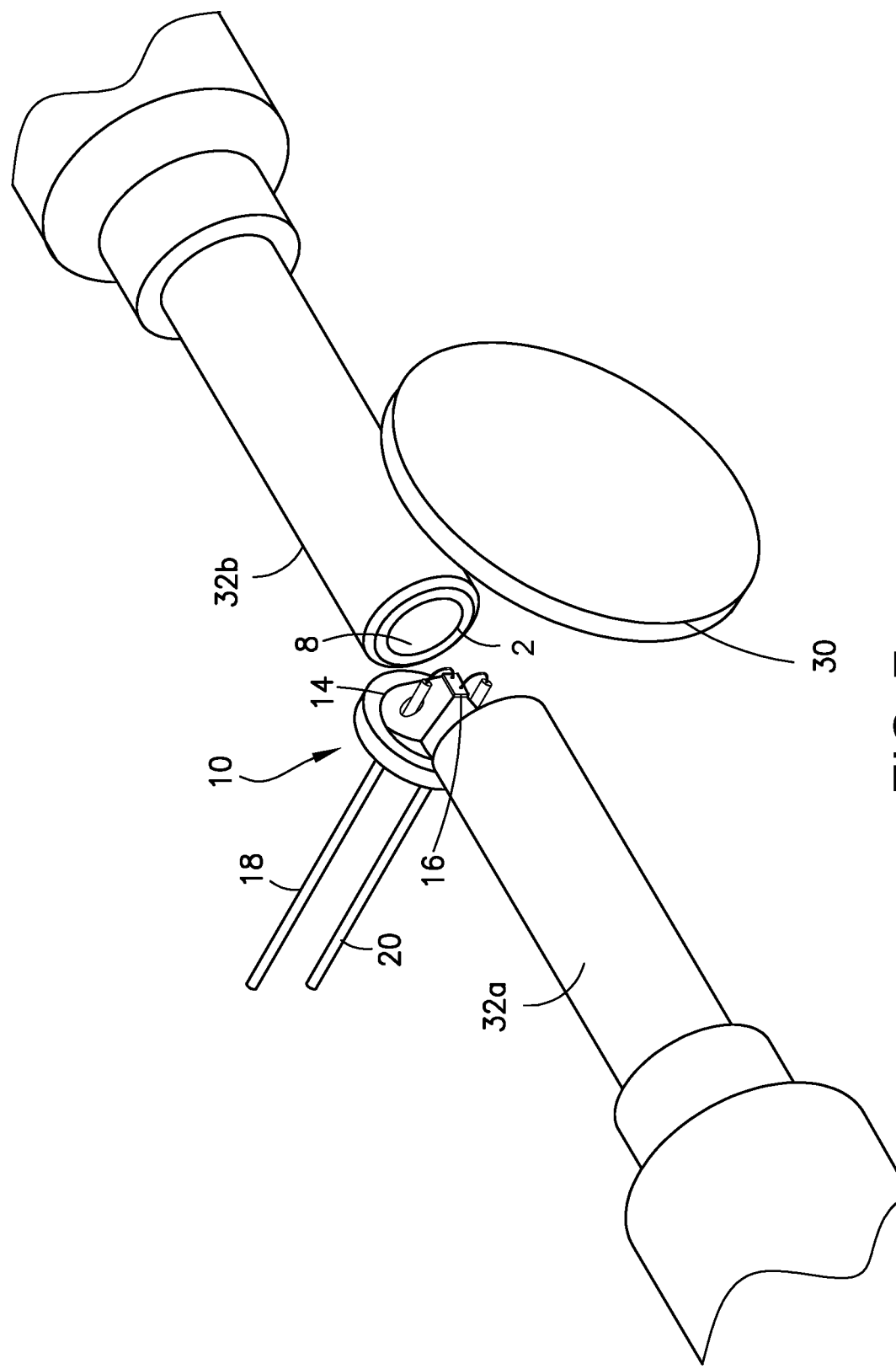
FIG. 7 is a diagram representing a three-dimensional view of the same components depicted in FIG. 6, but having a different viewpoint.
Figure 8:
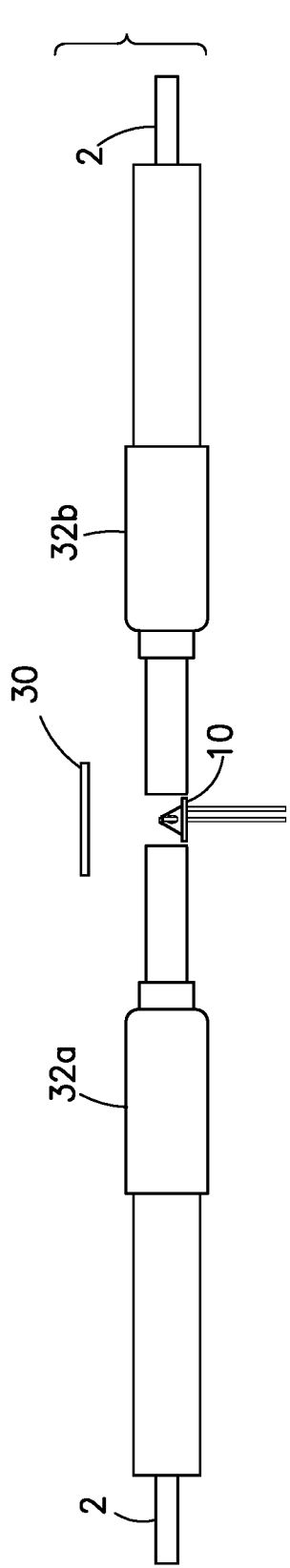
FIG. 8 is a diagram representing a side view of components depicted in FIGS. 6 and 7, again with the housing removed.

FIG. 7 is a three-dimensional view of the components depicted in FIG. 6. FIG. 8 is a diagram representing a side view of components depicted in FIGS. 6 and 7, again with the housing removed. FIG. 8 shows side-emitting optical fiber 2 (the same fiber or two different fibers) extended outside the fiber termini 32a and 32b. The exposed sections of. side-emitting optical fiber 2 emit UV-C laser light (as indicated by dashed arrows in FIG. 1) for the purpose of disinfection.

Figure 9:
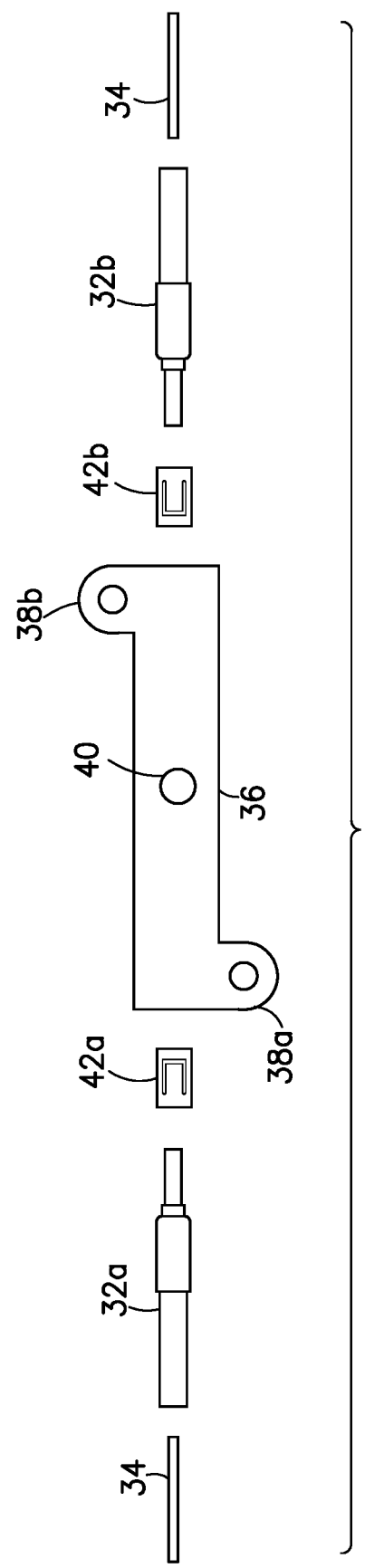
FIG. 9 is a diagram representing an exploded view of an optical subassembly housing and other optical subassembly components aligned along a center axis and in a disassembled state.

FIG. 9 is a diagram representing an exploded view of an optical subassembly housing 36 (hereinafter "OSA housing 36") and other optical subassembly components aligned along a center axis and in a disassembled state. The other components include the aforementioned end sections of side-emitting optical fiber 2 and termini 32a and 32b. Other optical subassembly components shown in FIG. 9 include terminus retainer clips 42a and 42b which are installed inside OSA housing 36 and are configured to retain termini 32a and 32b inside respective channels formed in OSA housing 36. The termini 32a and 32b are removable from the OSA housing 36 using a special removal tool.

To integrate all the components depicted in FIG. 9, the OSA housing 36 is designed to maintain proper alignment of the UV-C laser diode chip 16 with two end sections of side-emitting optical fiber 2 and with transparent window 30 which overlies the UV-C laser diode chip 16. In accordance with one proposed implementation, the OSA housing 36 is an aluminum module with openings at each end which respectively receive the termini 32a and 32b. In addition, the OSA housing 36 has an opening 40 on one face that receives the transparent window 30 and an opening (not visible in FIG. 9) on the opposite face through which the laser package 10 (see FIG. 8) is inserted into the OSA housing 36. The OSA housing 36 also has two flanges 38a and 38b on two sides for mounting onto a UV-C laser driver module (not shown in FIG. 9).

Figure 11:
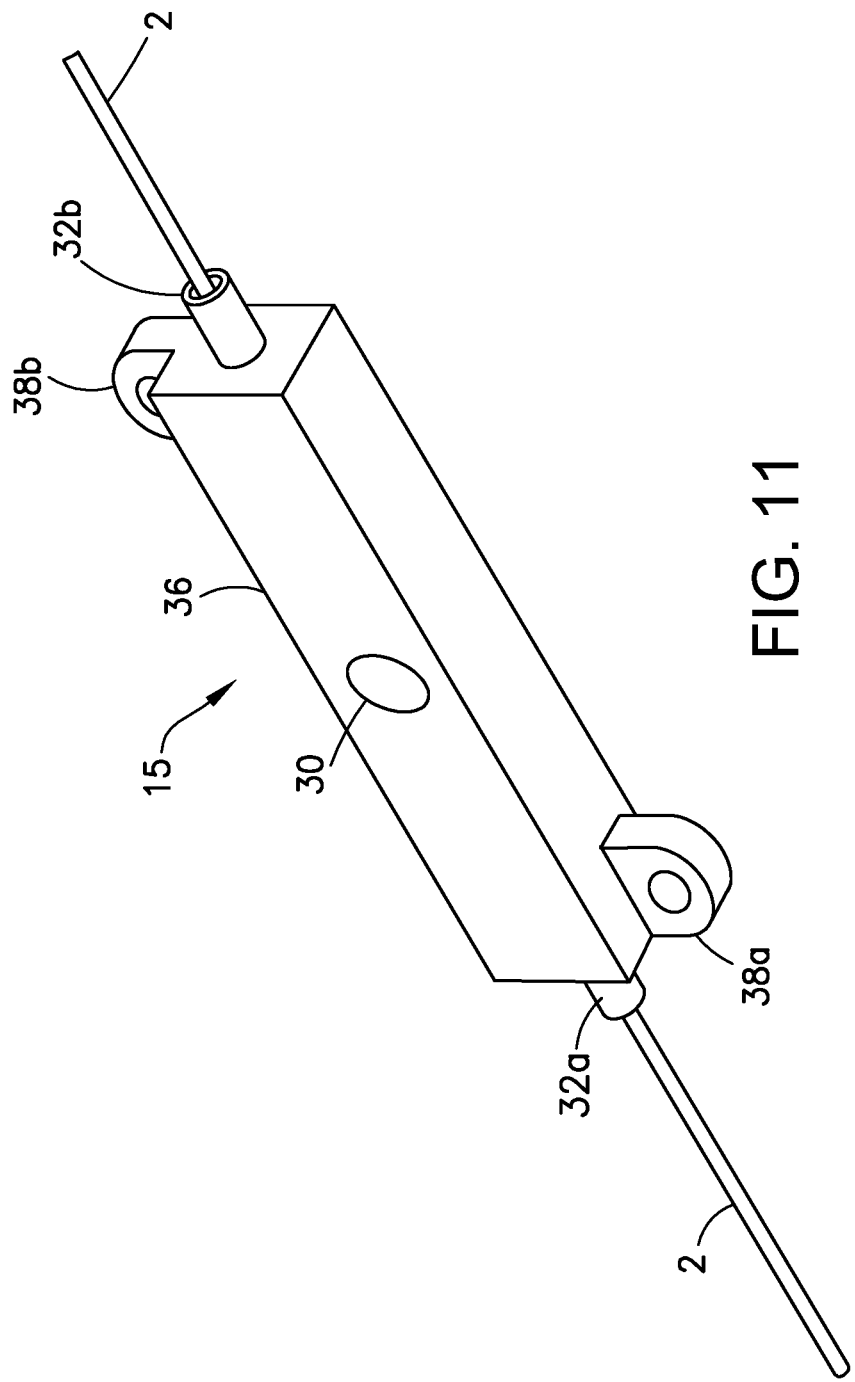
FIG. 11 is a diagram representing a three-dimensional view of the optical subassembly depicted in FIG. 10A.

FIG. 10A is a diagram representing a sectional view of an optical subassembly 15 that includes the components depicted in FIG. 9. Only the laser package 10 and side-emitting optical fiber 2 are not sectioned. FIG. 10B is a diagram representing a sectional view of the OSA housing 36 in isolation. FIG. 11 is a three-dimensional view of the optical subassembly 15 with exposed sections of side-emitting optical fiber 2 extending beyond the respective termini 32a and 32b.

FIG. 10A shows the inside view of the OSA housing 36 with all the components assembled together, whereas FIG. 10B shows the inside of OSA housing 36 with internal components removed. The termini 32a and 32b are retained in first and second channels 90 and 92 of the OSA housing 36 by the terminis retainer clips 42a and 42b. The laser package 10 is inserted into the OSA housing 36 via a third channel 94. The header base 12 of laser package is affixed to the top opening of the third channel 94. The transparent window 30 is affixed to a recessed top opening of the fourth channel 94. In accordance with one proposed implementation, both top openings are circular, as are the header base 12 and transparent window 30.

As best seen in FIG. 10B, the first and second channels 90 and 92 are mutually coaxial. Likewise, the third and fourth channels 94 and 96 are mutually coaxial. In accordance with one proposed implementation, the axis of the first and second channels 90 and 92 is perpendicular to the axis of the first and second channels 94 and 96. All of the four channels intersect at a central space 88 in the middle of the OSA housing 36. More specifically, each of the first and second channels 90 and 92 consists of two circular cylindrical sections having different diameters slightly greater than the outer diameters of respective sections of the termini 32a and 32b. The third channel 94 is circular cylindrical with recessed circular opening 40 having an offset that forms a seat 98 for the transparent window 30. The fourth channel 96 includes a conical section that connects the central space 88 to the recessed top opening. The diameter of the conical section of the fourth channel 96 increases in the direction from the central space 88 to the transparent window 30 (see FIG. 10A).

In accordance with the configuration depicted in FIG. 10A, the UV-C laser diode chip 16 is situated precisely at the center of the central space 88. More specifically, the header base 12 of the laser package 10 is attached to the top opening of the third channel 94 of the OSA housing 36 by high-temperature, non-conductive, space-grade epoxy. The transparent window 30 is attached to the recessed top opening of the fourth channel 96 of the OSA housing 36 by space-grade optically transparent epoxy. The transparent window 30 is located above the UV-C laser diode chip 16 to facilitate observation of the laser diode chip position during the process of assembling the optical subassembly 15. The transparent window 30 also allows residual UV-C laser light emitted from the top of the UV-C laser diode chip 16 to exit the OSA housing 36 to provide additional virus-disinfecting UV-C laser light in the space and on surfaces in the path of that propagating light.

When all the components are assembled together as shown in FIG. 10A, the two edges of the UV-C laser diode chip 16 are optimally aligned to the two end sections 34 of side-emitting optical fiber respectively disposed inside the termini 32a and 32b. The transparent window 30 is also at a position which maximizes the UV-C laser light collected from the top of the laser diode chip 16.

Figure 12:
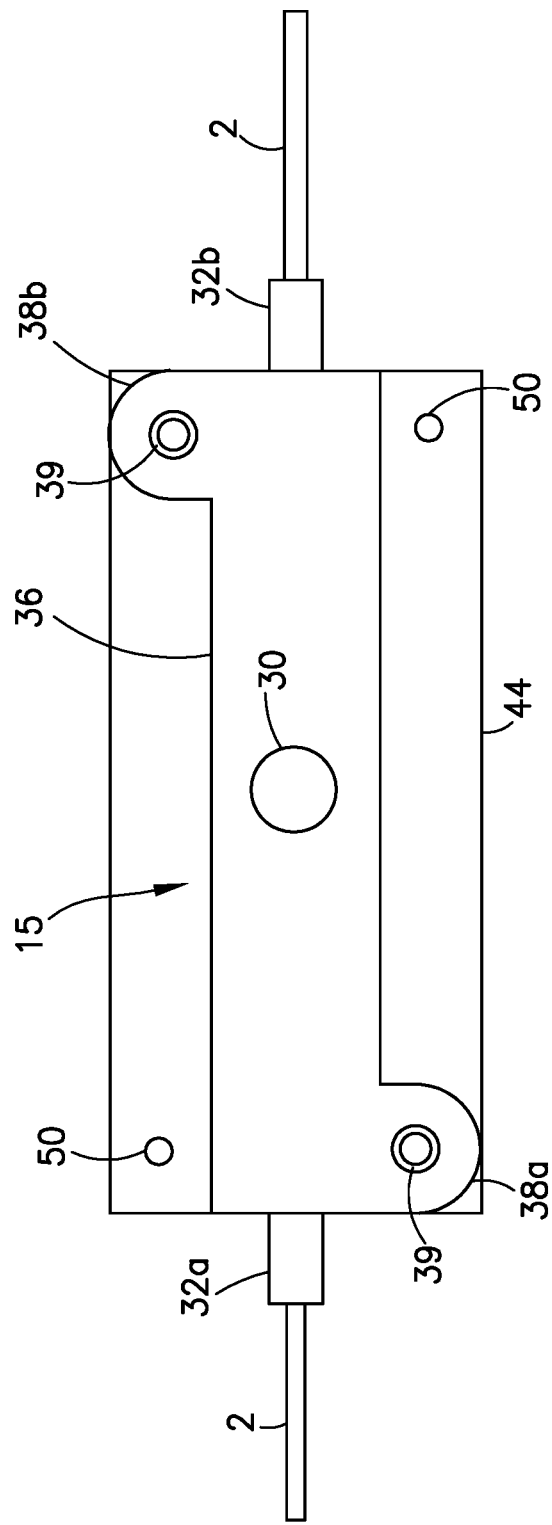
FIG. 12 is a diagram representing a top view of the optical subassembly depicted in FIG. 11.

FIG. 12 is a diagram representing a top view of the optical subassembly 15 attached to an electronics housing 44. First, the holes in the flanges 38a and 38b of the optical subassembly 15 are aligned with respective mounting holes 50 formed in the electronics housing 44. A pair of fasteners 39 are then inserted in the aligned holes.

Figure 13:
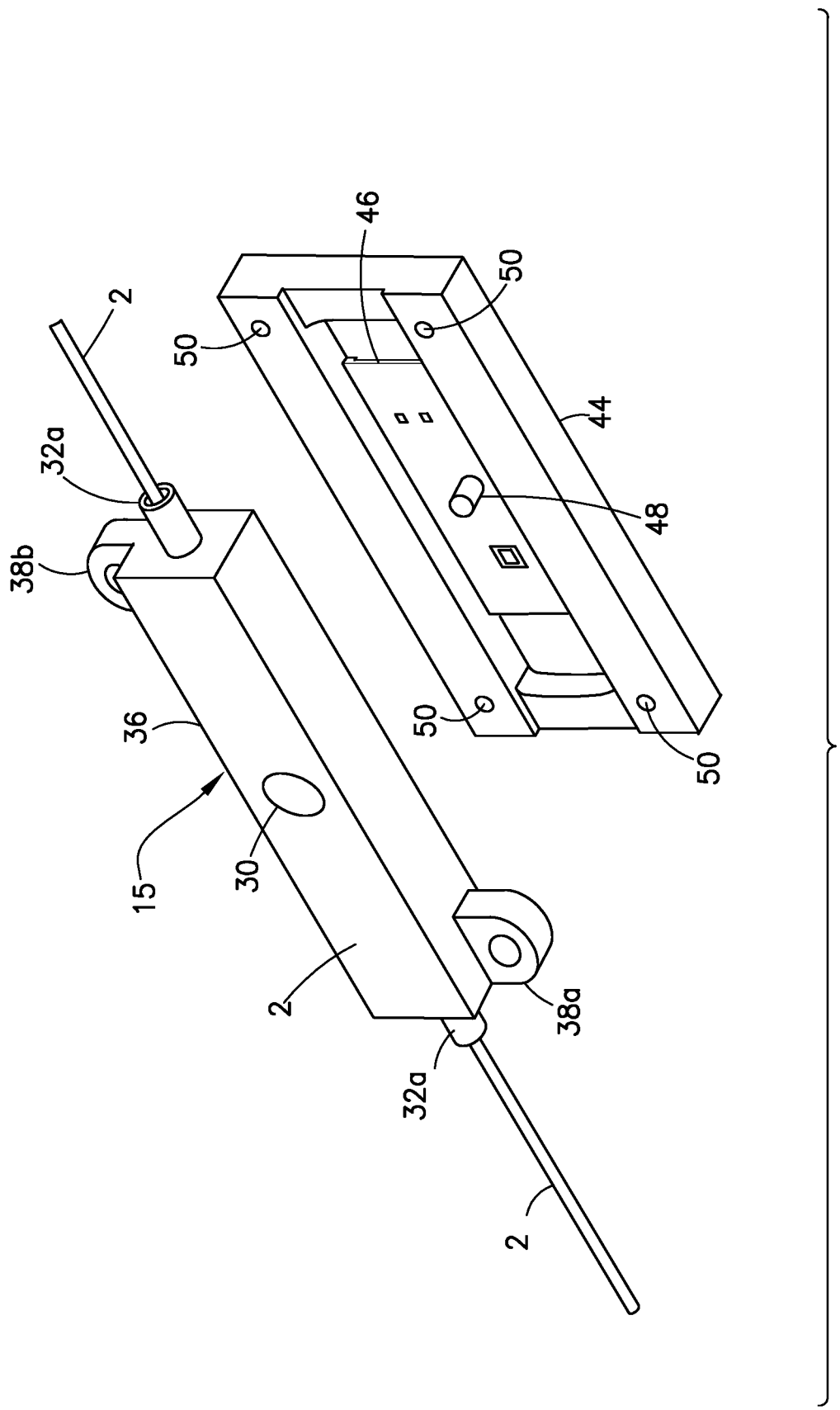
FIG. 13 is a diagram representing a three-dimensional view of the optical subassembly depicted in FIG. 12 and an electronics housing prior to their assembly.
Figure 14:
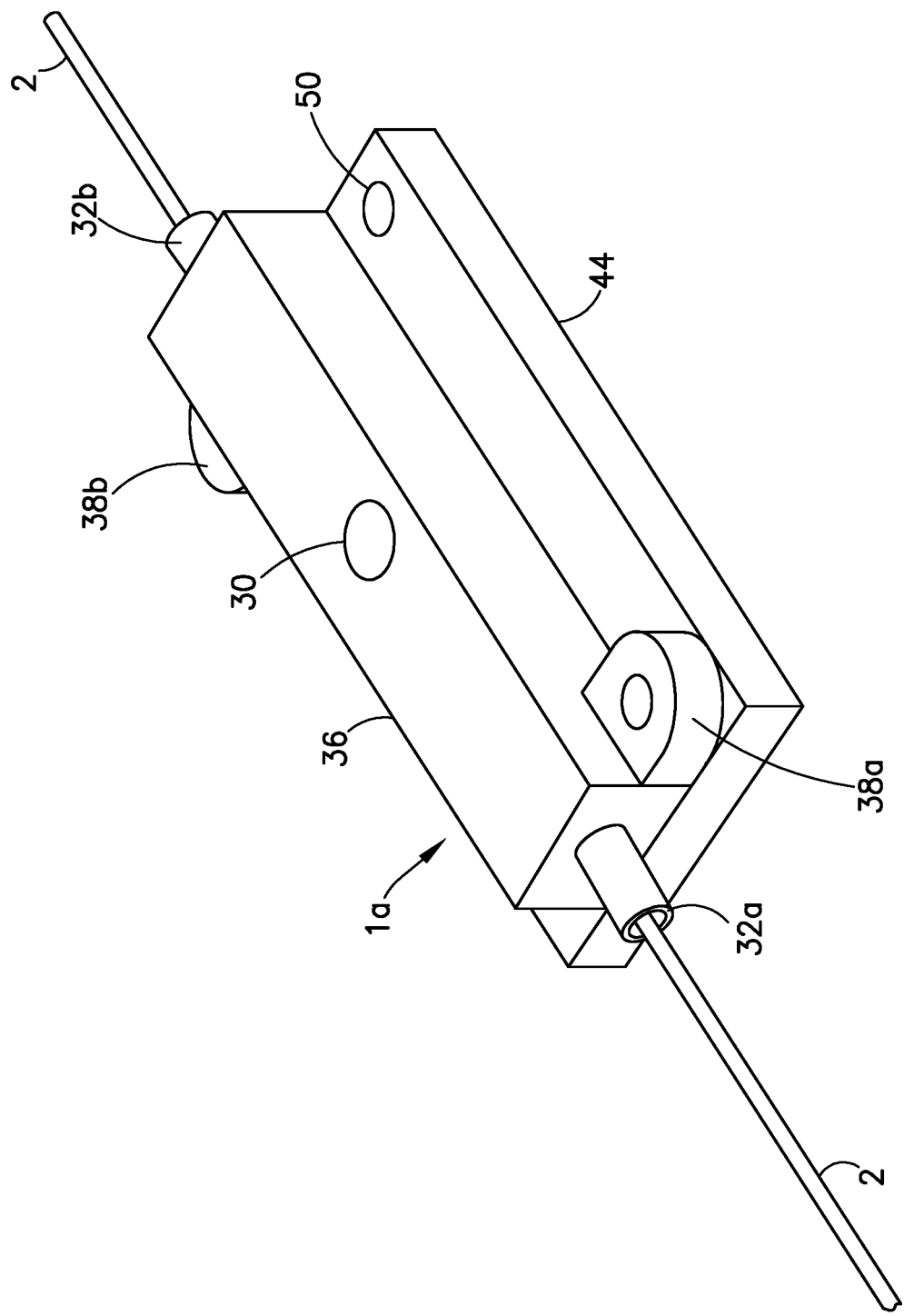
FIG. 14 is a diagram representing a three-dimensional view of the optical disinfection system formed when the optical subassembly and electronics housing depicted in FIG. 13 are assembled.

FIG. 13 is a diagram representing a three-dimensional view of the optical subassembly 15 and electronics housing 44 prior to their assembly. In accordance with one proposed implementation, the electronics housing 44 is an aluminum module which contains a UV-C laser driver electronics printed wiring board 46 (hereinafter "PWB 46"). A three-pin socket 48 is located in the center of PWB 46 to connect the three pins of the UV-C laser package 10 to the electronic components on the PWB 46. The electronics housing 44 also has four mounting holes 50 at the four corners of the housing. Two of the four mounting holes 50 are used to mount the optical subassembly 15 to electronics housing 44; the other two mounting holes 50 are used to mount the completed assembly onto an airplane ceiling or other external fixture, such as a window, a door, a tray, and an overhead storage bin. FIG. 14 is a diagram representing a three-dimensional view of the optical subassembly 15 and electronics housing 44 after their assembly to form an optical disinfection system 1a, but before being mounted to an external fixture.

Figure 15:
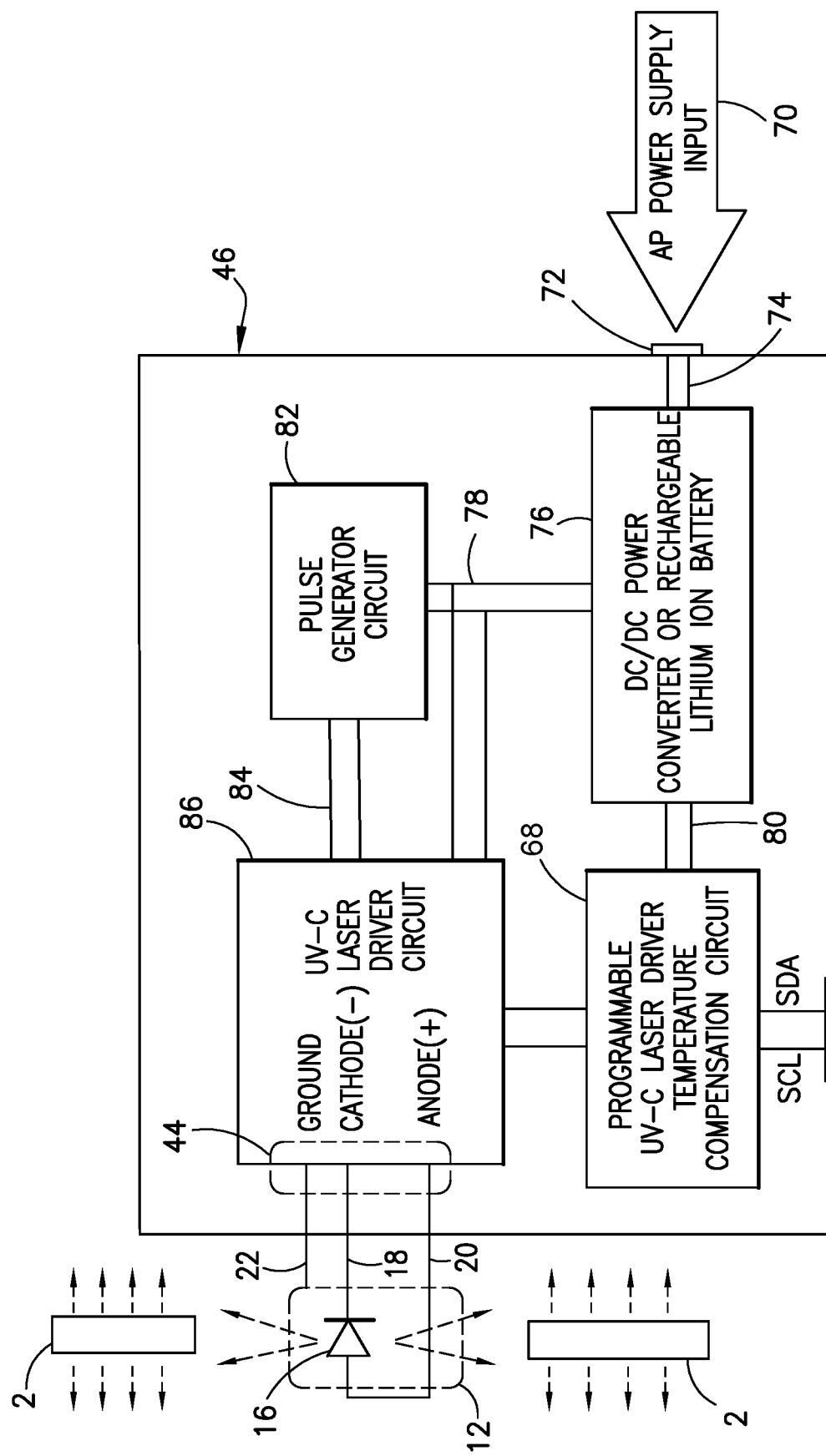
FIG. 15 is a block diagram identifying laser driver electronic circuit components on the printed wiring board of the optical disinfection system depicted in FIG. 14 in accordance with one embodiment.

FIG. 15 is a block diagram identifying laser driver electronic circuit components on the PWB 46 of the optical disinfection system 1a depicted in FIG. 14 in accordance with one embodiment. The UV-C laser diode chip 16 is connected to the PWB 46 through the three-pin socket 48. The laser diode chip's p-contact is connected to the anode pin 20, the laser diode chip's n-contact is connected to the cathode pin 18, and the ground pin 22 is connected to the PWB common ground plane. The pulse generator circuit 82 generates high-speed low-duty-cycle voltage pulses which are input to the UV-C laser driver circuit 86 via high-speed signal line 84. The UV-C laser driver circuit 86 converts the voltage pulses from the pulse generator circuit 82 to current pulses which drive the UV-C laser diode chip 16 to generate high-speed low-duty-cycle UV-C light pulses to perform disinfection.

The UV-C laser driver circuit 86 is also connected to the UV-C laser driver temperature compensation circuit 90, which is configured to stabilize the UV-C laser light output of the UV-C laser diode chip 16 over a temperature range of −40° C. to 100° C. The UV-C laser driver temperature compensation circuit 90 circuit is programmable through a two-pin I²C serial interface. The two pins Serial Data (SDA) and Serial Clock (SCL) are connected to an external computer (not shown in FIG. 14) through a micro-USB connector 66. With this I²C interface, the UV-C laser light output power will remain constant over a wide avionic temperature range using an externally loaded software program in its memory.

The pulse generator circuit 82, UV-C laser driver circuit 86, and UV-C laser driver temperature compensation circuit 90 receive DC power from a DC/DC power converter 76 via DC power supply lines 78 and 80. The DC/DC power converter 76 is connected to receive the airplane's DC power supply input 70 through an avionics qualified power supply connector 72 and via DC power supply line 74. Because standard airplane DC power supply is 28 V, and the circuits inside the PWB 46 need 5 V (or 3.3 V) power supplies, the DC/DC converter's function is to convert the 28-V DC power supply input 70 from the airplane to a 5-V (or 3.3-V) power supply.

Using the PWB design depicted in FIG. 14 to drive UV-C laser pulses at a 10% duty cycle, the UV-C laser's peak optical power will be 10 times higher than the continuous wave optical power. This is a tenfold increase in UV-C optical power to disinfect surfaces in an airplane. The pulse generator circuit 82 provides high-speed voltage pulses with pulse width of 100 nsec or less. Thus, the UV-C laser diode chip 16 outputs high-speed and high-peak-power UV-C laser light which is effective to disinfect a virus because 100 nsec is much faster than the virus replication time. The virus would be killed by the UV-C laser light from the laser before the virus can replicate.

If airplane DC power is not available, a long-operating-time lithium ion battery may be substituted in place of the DC/DC power converter 76 in the PWB design. Using the lithium ion battery, the UV-C optical subassembly can be operated without any external electrical wire connection.

Figure 16:
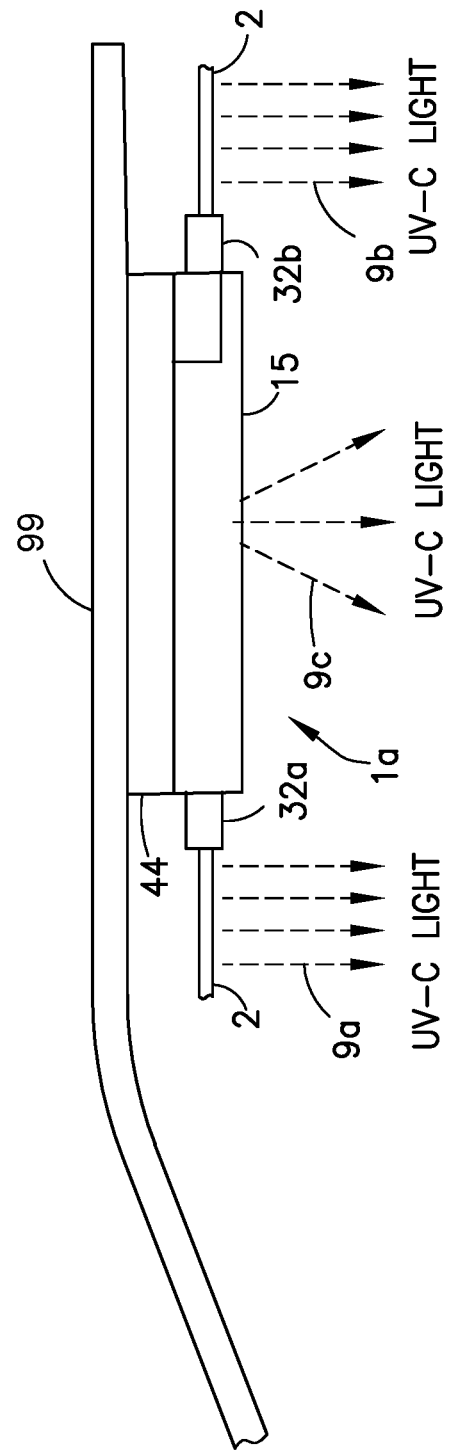
FIG. 16 is a diagram representing a side view of the optical disinfection system depicted in FIG. 14 installed on the cabin ceiling of an airplane.

FIG. 16 shows a side view of the UV-C optical subassembly 15 with the electronics housing 44 installed upside down on the ceiling 99 of an airplane cabin. The UV-C laser light 9a and 9b is emitted from side-emitting optical fiber 2 (a single fiber in the shape of a loop or two separate fibers). Also residual UV-C laser light 9c is emitted from the transparent window 30 (not visible in FIG. 16) in the middle of the UV-C optical subassembly 15.

Figure 17:
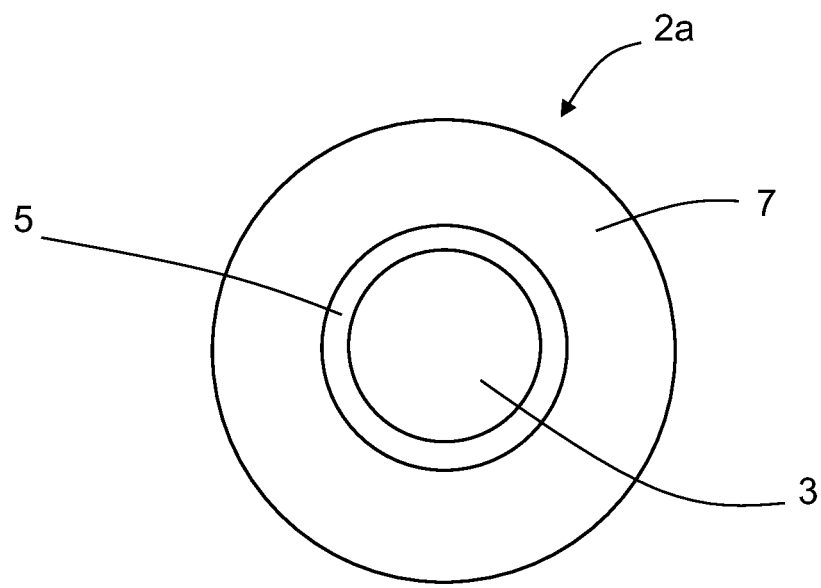
FIG. 17 is a diagram representing an end view of one type of side-emitting optical fiber.

FIG. 17 is a diagram representing an end view of one type of side-emitting step-index optical fiber 2a which is suitable for use in the optical disinfection system disclosed herein. A step-index optical fiber has a refractive index profile characterized by a uniform refractive index within the core and a sharp decrease in refractive index at the core-cladding interface so that the cladding has a lower refractive index. The side-emitting step-index optical fiber 2a shown in FIG. 17 has a scattering region 5 made from a glass with embedded scattering particles (not shown in FIG. 17) and located between the core 3 and cladding 7. The scattering region 5 surrounds the core 3. Some of the light propagating through the core 3 is scattered radially outward through the cladding 7 due to the presence of the scattering particles.

Figure 18:
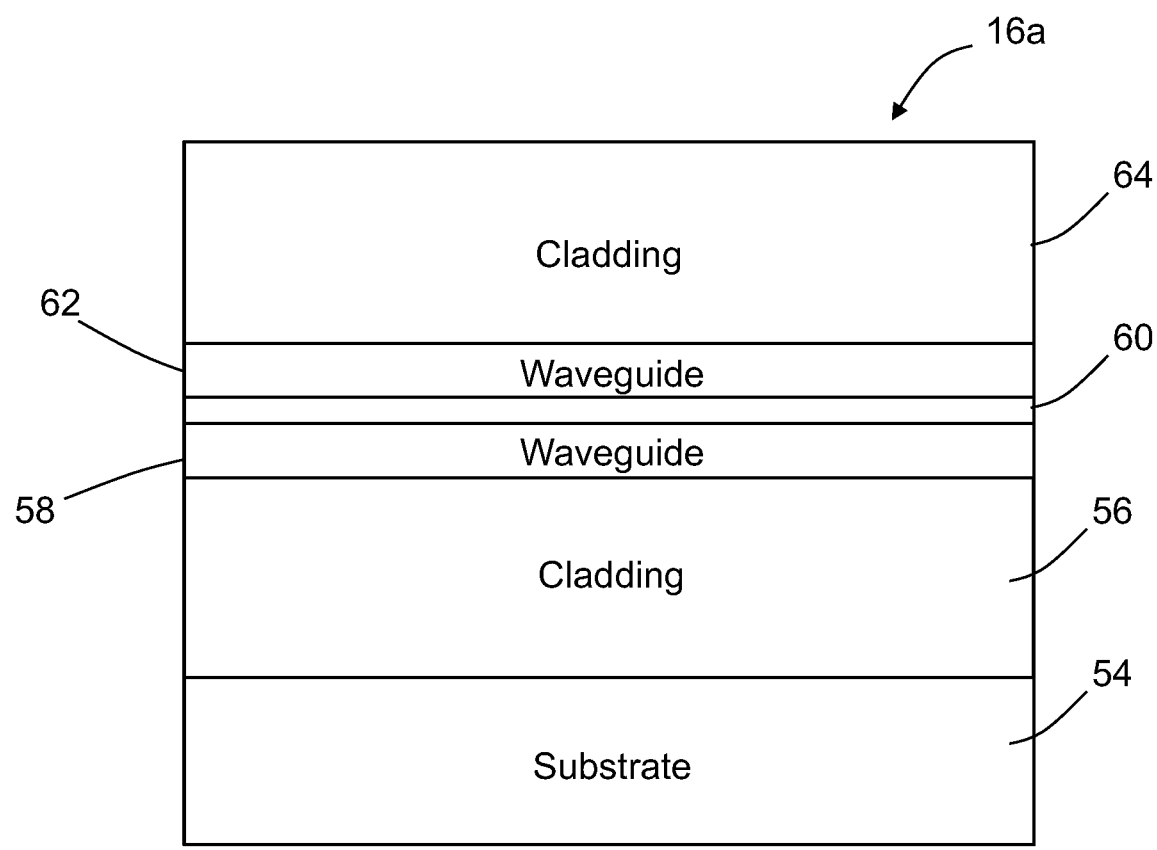
FIG. 18 is a diagram representing an end view showing some layers in a UV-C edge-emitting laser diode semiconductor chip.

FIG. 18 is a diagram representing an end view showing some layers in a UV-C edge-emitting laser diode semiconductor chip 16a. Semiconductor lasers are typically fabricated on a wafer by growing layered semiconductor material on a substrate 54 to form an epitaxial structure having an active layer 60 parallel to the substrate surface. The wafer is then processed with a variety of semiconductor processing tools to produce a laser optical cavity incorporating the active layer 60 and metallic contacts (not shown in FIG. 18) attached to the semiconductor material. Laser mirror edges typically are formed at the ends of the laser cavity by cleaving or etching. Within the edge-emitting laser structure, the laser light is guided in a p-side waveguide 62 and an n-side waveguide 58 which sandwich the active layer 60. The layers in UV-C edge-emitting laser diode semiconductor chip 16a further include n-side cladding 56 grown on substrate 54 and p-side cladding 64 grown on p-side waveguide 62.

In 2019, a description of a laser structure that generates UV-C light effectively, emitting at 271.8 nm, was published by Nagoya University and Asahi Kasei Corporation. The key technical accomplishment of this UV-C laser development is a high-quality single-crystal aluminum nitride (AlN) substrate 54 and the aluminum composition gradient in the cladding (optical confinement) layers, which minimize defects in the active layer 60 of the laser diode. More specifically, the reported laser structure had an n-side cladding 56 made from $Al_{0.7}Ga_{0.3}N$, an n-side waveguide 58 made from $Al_{0.63}Ga_{0.37}N$, an active layer 60 in the form of a single quantum well, a p-side waveguide 62 made from $Al_{0.63}Ga_{0.37}N$, and a p-side cladding 64 which is distributed polarization doped. More details of this laser structure are provided by Zhang et al. in: "A 271.8 nm deep-ultraviolet laser diode for room temperature operation," Applied Physics Express 12, 124003 (2019), published by The Japan Society of Applied Physics.

In summary, the optical subassembly design proposed herein may be used in an UV-C virus optical disinfection system inside an airplane. The proposed optical subassembly has a high peak output power and high reliability. This optical subassembly can be operated with either a standard airplane 28-V power supply or a battery in case an external power supply is not available or feasible.

While an optical subassembly having side-emitting optical fiber optically coupled to a UV-C laser diode has been described with reference to various embodiments, it will be understood by those skilled in the art that various changes may be made and equivalents may be substituted for elements thereof without departing from the teachings herein. In addition, many modifications may be made to adapt the concepts and reductions to practice disclosed herein to a particular situation. Accordingly, it is intended that the subject matter covered by the claims not be limited to the disclosed embodiments.

The invention claimed is:

1. An optical subassembly comprising:
   a housing that defines a central space and first, second, and third channels which extend from the central space;
   a laser package affixed to the third channel and comprising a UV-C laser diode chip disposed in the central space and having first and second edges;
   a first end section of side-emitting optical fiber retained in the first channel and having a first end face which confronts the first edge; and
   a second end section of side-emitting optical fiber retained in the second channel and having a second end face which confronts the second edge.

2. The optical subassembly as recited in claim 1, wherein the housing further defines a fourth channel which extends from the central space and has an offset, further comprising a transparent window seated on the offset.

3. The optical subassembly as in claim 1, wherein the laser package further recited comprises:
   a header base having first and second throughholes;
   a ground pin having one end connected to the header base;
   a heat sink having a top, a base, and first and second throughholes that pass through the base and not the top, the base of the heat sink being attached to the header base and the UV-C laser diode chip being attached to the top of the heat sink;
   an anode pin that passes through the first throughholes in the header base and heat sink with electrical insulation between the anode pin and the header base and heat sink;
   a cathode pin that passes through the second throughholes in the header base and heat sink with electrical insulation between the cathode pin and the header base and heat sink;
   a first wire that connects the UV-C laser diode chip to the anode pin; and
   a second wire that connects the UV-C laser diode chip to the cathode pin.

4. The optical subassembly as recited in claim 3, wherein the top of the heat sink has a first surface area and the base of the heat sink has a second surface area greater than the first surface area.

5. The optical subassembly as recited in claim 1, wherein the UV-C laser diode chip comprises a quantum well and first and second waveguides disposed on opposite sides of the quantum well.

6. A laser package comprising:
   a header base having first and second throughholes;
   a ground pin having one end connected to the header base;
   a heat sink having a top, a base, and first and second throughholes that pass through the base and not the top, the base of the heat sink being attached to the header base;
   an anode pin that passes through the first throughholes in the header base and heat sink with electrical insulation between the anode pin and the header base and heat sink;
   a cathode pin that passes through the second throughholes in the header base and heat sink with electrical insulation between the cathode pin and the header base and heat sink;
   a laser diode chip attached to the top of the heat sink, the laser diode chip being configured to emit UV-C laser light;
   a first wire that connects the UV-C laser diode chip to the anode pin; and
   a second wire that connects the UV-C laser diode chip to the cathode pin.

7. The laser package as recited in claim 6, wherein the top of the heat sink has a first surface area and the base of the heat sink has a second surface area greater than the first surface area.

8. The laser package as recited in claim 6, wherein the UV-C laser diode chip comprises an edge-emitting laser diode.

9. The laser package as recited in claim 8, wherein the edge-emitting laser diode comprises a quantum well and first and second waveguides disposed on opposite sides of the quantum well.

10. An optical disinfection system comprising:
an electronics housing;
a printed wiring board attached to the electronics housing and comprising a socket;
a laser package plugged into the socket of the printed wiring board, the laser package comprising a laser diode chip configured to emit UV-C laser light;
a first end section of a side-emitting optical fiber having a first end face;
a first terminus surrounding the first end section;
a second end section of a side-emitting optical fiber having a second end face;
a second terminus surrounding the second end section; and
an optical subassembly housing attached to the electronics housing, the optical subassembly housing having a first channel in which the first terminus is seated and a second channel in which the second terminus is seated.

11. The optical disinfection system as recited in claim 10, wherein the first and second end faces are end faces of a single side-emitting optical fiber.

12. The optical disinfection system as recited in claim 10, wherein the first and second end faces are end faces of respective side-emitting optical fibers.

13. The optical disinfection system as recited in claim 10, wherein the optical subassembly housing has an opening overlying the laser diode chip, the optical disinfection system further comprising a transparent window seated in the opening.

14. The optical disinfection system as recited in claim 10, wherein the printed wiring board further comprises a pulse generator that is configured to generate pulses and a laser driver circuit that is connected to receive the pulses generated by the pulse generator.

15. The optical disinfection system as recited in claim 10, wherein the laser package further comprises:
a header base having first and second throughholes;
a ground pin having one end connected to the header base;
a heat sink having a top, a base, and first and second throughholes that pass through the base and not the top, the base of the heat sink being attached to the header base and the laser diode chip being attached to the top of the heat sink;
an anode pin that passes through the first throughholes in the header base and heat sink with electrical insulation between the anode pin and the header base and heat sink;
a cathode pin that passes through the second throughholes in the header base and heat sink with electrical insulation between the cathode pin and the header base and heat sink;
a first wire that connects the UV-C laser diode chip to the anode pin; and
a second wire that connects the UV-C laser diode chip to the cathode pin.

16. The optical disinfection system as recited in claim 15, wherein the laser diode chip comprises an edge-emitting laser diode having first and second edges which respectively confront the first and second end faces.

17. An assembly comprising:
a printed wiring board comprising a socket;
a laser package plugged into the socket of the printed wiring board, the laser package comprising an UV-C laser diode having first and second edges;
a first end section of side-emitting optical fiber having a first end face;
a second end section of side-emitting optical fiber having a second end face; and
a housing which is configured to maintain the laser package and the first and second end sections of side-emitting optical fiber in fixed positional relationships such that the first end face confronts the first edge and the second end face confronts the second edge.

18. The assembly as recited claim 17, wherein the first and second end faces are end faces of a single side-emitting optical fiber.

19. The assembly as recited in claim 17, wherein the first and second end faces are end faces of respective side-emitting optical fibers.

20. The assembly as recited in claim 17, wherein the printed wiring board further comprises a pulse generator that is configured to generate pulses and a laser driver circuit that is connected to receive the pulses generated by the pulse generator and drive UV-C laser light emission by the UV-C laser diode.

* * * * *